United States Patent
Zika et al.

[11] Patent Number: 6,040,912
[45] Date of Patent: Mar. 21, 2000

[54] METHOD AND APPARATUS FOR DETECTING PROCESS SENSITIVITY TO INTEGRATED CIRCUIT LAYOUT USING WAFER TO WAFER DEFECT INSPECTION DEVICE

[75] Inventors: Steven J. Zika, Fremont; C. Bradford Hopper, San Francisco, both of Calif.

[73] Assignee: Advanced Micro Devices, Inc., Sunnyvale, Calif.

[21] Appl. No.: 09/163,314

[22] Filed: Sep. 30, 1998

[51] Int. Cl.[7] .................................................. G01B 11/00
[52] U.S. Cl. ......................................... 356/394; 356/237.5
[58] Field of Search ............................ 356/237.1, 237.4, 356/237.5, 239.3, 394

[56] References Cited

U.S. PATENT DOCUMENTS

| | | | |
|---|---|---|---|
| 4,209,257 | 6/1980 | Uchiyama et al. | 356/394 |
| 4,579,455 | 4/1986 | Levy et al. | 356/394 |
| 4,680,627 | 7/1987 | Sase et al. | 356/394 |
| 4,701,859 | 10/1987 | Matsuyama et al. | 356/394 |
| 4,718,767 | 1/1988 | Hazama | 356/394 |
| 4,774,461 | 9/1988 | Matsui et al. | 356/394 |
| 4,778,745 | 10/1988 | Leung | 356/394 |
| 4,860,371 | 8/1989 | Matsuyama et al. | 356/394 |
| 5,767,974 | 6/1998 | Higashiguchi et al. | 356/394 |

*Primary Examiner*—Hoa Q. Pham

[57] ABSTRACT

A method and apparatus for detecting random layout structures sensitive to process induced pattern errors in semiconductor device manufacturing applies a first manufacturing process to a first wafer containing semiconductor devices. A second manufacturing process is applied to a second wafer containing semiconductor devices. The second manufacturing process is similar to, but different from the first manufacturing process. The first and second wafers are compared by image subtraction to detect systematic pattern defects in the semiconductor devices of one of the first and second wafers. After differences are detected, the layout is examined to determine whether the difference represents a defect. If so, the design rules of the layout can be changed to accommodate a wider process variation and improve processing yield.

11 Claims, 4 Drawing Sheets

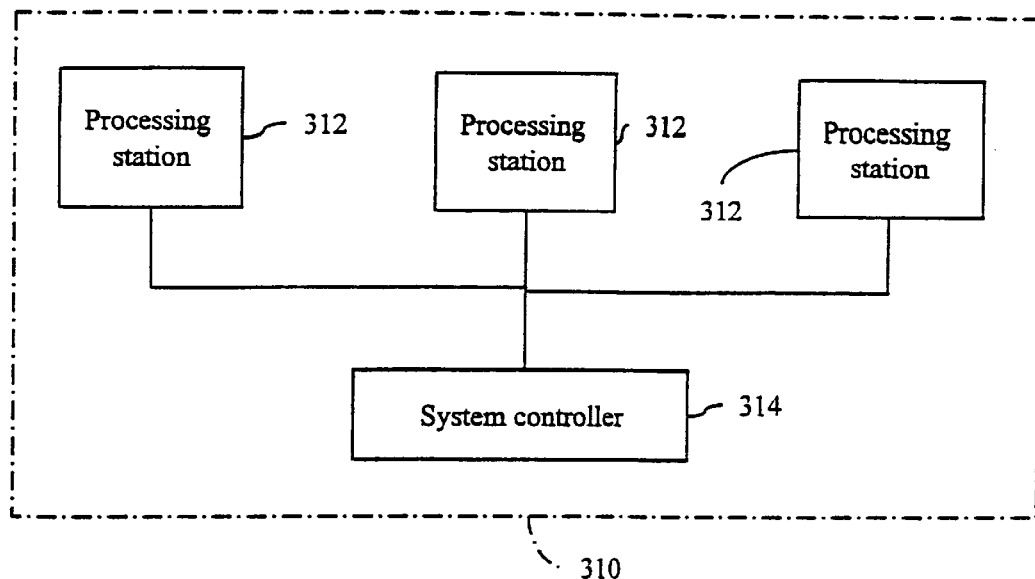
Fig. 3
Fig. 4
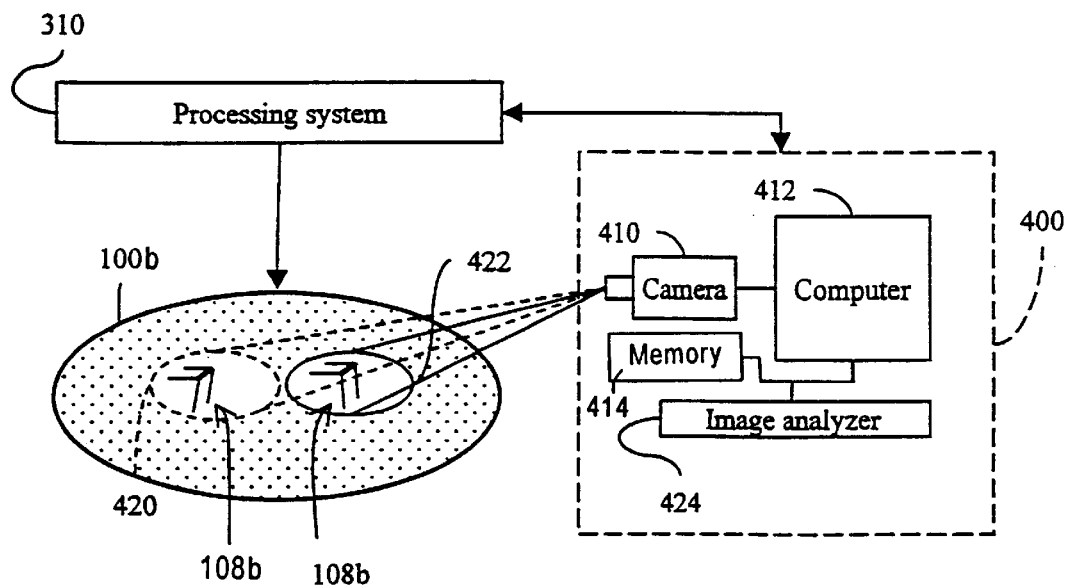

6,040,912

METHOD AND APPARATUS FOR DETECTING PROCESS SENSITIVITY TO INTEGRATED CIRCUIT LAYOUT USING WAFER TO WAFER DEFECT INSPECTION DEVICE

TECHNOLOGICAL FIELD OF THE INVENTION

The present invention relates to the field of manufacturing products, such as semiconductor chips, and more particularly, to a method and apparatus for detecting systematic pattern defects related to the manufacturing process.

DESCRIPTION OF RELATED ART

The manufacture of wafers containing semiconductor devices requires a number of discrete processing steps to produce a packaged semiconductor circuit device from raw semiconductor material. The starting substrate is usually a slice of single crystal silicon referred to as a wafer 100 (FIG. 1) on which a plurality of dies 104 are formed by a semiconductor processing method. There are a number of various semiconductor processing methods, such as etching, oxidation, deposition (e.g., chemical vapor or physical), sputtering, diffusion, ion implantation, lithography, each of which typically has multiple steps. The semiconductor processing methods are used to form regular arrays 106 (FIG. 2A) of integrated circuits, particularly when the processing method is used to create a memory device or the cache of a microprocessor device. FIG. 2A illustrates that the circuits are typically created in a die, such as 104a, from a plurality of conductive paths 109 that together form a layout structure 108a. Layout structures 108a, 108a', 108a" are shown in FIG. 2A only as partial views of the exemplary conductive paths 109 that comprise a much more complicated circuit configuration (not shown). The layout structures 108a may be considered a cell, for purposes of discussion.

Each particular conductive path 109 of layout structure 108a may be affected differently by the various processing methods. Using the etching step as an example, it is widely known that different design layout structures (generally referred to with numeral 108) have different sensitivities to local etch/polish/masking steps, as well as to variances in the loading and proximity of the structures (i.e. paths 109) to one another. These sensitivities may result in unintended processing errors which form unwanted effects. Examples of these unwanted effects include a bridge 110 (FIG. 2B) between paths 109 of layout structure 108b that are intended to be separate, an open area (not shown) between paths 109 which are intended to be contiguous, a differential layer thickness (not shown) due to non-uniform polish, an under-etched contact (not shown), or any number of unwanted effects which are referred to as "systematic pattern errors".

Although there is a general understanding that areas densely packed with layout structures will, for example, etch differently than loosely packed areas, there is currently no automated means for detecting which areas are most susceptible to systematic pattern errors. This is especially a problem in inherently random structures where the density of layout structures varies such that no particular area can be identified as more problematical than another. This problem is exacerbated by the current state of the art in layout methodology which allows for automated placement of paths 109 (and spaces between the paths) of layout structures 108 to be accomplished using predetermined design rules. If a particular structure 108 which tends to be problematic due its location next to other structures is not explicitly excluded from a design rule, unwanted failures (e.g., shorts or unconnected contacts) might occur during the actual production of the semiconductor wafer. Further complicating the matter is the fact that the layout engineers may not be aware of the existence of such problems.

Currently, systematic pattern errors in layout structures randomly placed according to automated design rules can only be found by manual optical inspection or examination of electrical performance of test structures in these areas. Other wafer inspection tools which are useful for detecting non-systematic defects, such as particulate defects or non-repeating improperly formed patterns, cannot be used to find repeating failures like bridge 110.

Turning to FIG. 2B for example, two paths 109 of layout structure 108a can be randomly laid out by automated design rules repeatedly across die 104a. If the actual manufacturing process used provides the intended result, the structure appears as depicted by 108a in FIG. 2a. However, if there are variances in the processing method, such as a slightly longer etch time, bridge 110 might be formed to yield structure 108b which would be located in each die 104a, 104b, and 104c on the wafer. Alternatively, in an attempt to avoid creating bridge 110, slightly less etch time might be used, and an open area (not shown) may be formed in all dies 104 on the wafer.

Assuming that the automated design rules create a die with thousands of layout structures intended to be like structure 108a, but the die also included hundreds of thousands of other structures, it is very difficult to determine which of the structures 108a causes a failure in a circuit. Furthermore, certain structures 108a may exhibit errors only when placed adjacent to certain other circuit structures, but the automated design rules may actually specify this type of failing combination which repeats itself in random locations across the die 104a.

Current state of the art defect inspection tools typically use two image subtraction methods for inspecting areas of integrated circuits. The first, called cell-to-cell, is used when the area being inspected can be subdivided into small areas which contain identical structures 108a laid out in a repetitive array 106 such as the core of a memory device or the cache of a microprocessor device. The second, called die-to-die, is used when the area being inspected does not repeat over significant distances and thus cannot be subdivided into identical cells so the entire die 104a is compared to identical dies 104b, 104c, 104d. Die-to-die defect detection is typically used to find random, non-repeating defects.

In cell-to-cell mode, an image of array 106 of the repeating cell structure 108a is acquired and compared to another image of structure 108a in array 106 in a nominally identical neighboring region. These images are compared, and where they differ, the inspection tool identifies that location as a defect. In the case of FIG. 2A, no defect would be detected by this method because no errors exist when comparing the images of identical structures 108a. However, the cell-to-cell mode would also not detect errors when comparing images of the structures 108b in FIG. 2B if those structures were contained in array 106. This is because in the cell-to-cell mode, repeating structure is not detected as an error. This cell-to-cell defect detection process continues as the entire repeating array 106 is stepped through, comparing each cell to its nearest neighbor and assigning defect locations.

In die-to-die mode, an image of the entire die 104a, or subset thereof, is compared to a nominally identical image in the neighboring die 104b. The same type of image comparison is performed as in the cell-to-cell mode. The die-to-die process requires much greater memory capacity than the cell-to-cell process, since the image of an entire die is stored for later comparison, and not just a cell within that die.

The two defect detection methods discussed immediately above are scaled versions of one another with the requirement that the two images being compared must be substantively identical. Both techniques are useful for detecting particulates, scratches and processing-induced defects like missing features, residual photoresist etc. However, any feature which is present in both images being compared will not be detected, as only differences are detectable. Layout specific process induced defects (e.g., repeating systematic pattern errors) fall into this category.

Another problem with the known methods is that it is impossible to detect layout errors that occur in each die across a wafer. In other words, assuming a random layout and a manufacturing process step with parameters that cause a defect (such as bridging) for that layout, every die on that wafer will contain that defect. A die-to-die inspection, searching for differences between dies by the image subtraction method, will not recognize the bridge as a defect since it appears in each die.

SUMMARY OF THE INVENTION

There is therefore a need for a method and an apparatus for detecting repeating systematic pattern defects in integrated circuits. There is another need for a method and apparatus that does not rely on manual optical inspection or examination of electrical performance of test structures in these areas to detect repeating systematic pattern defects.

The following described method allows the use of these conventional inspection tools to detect layout structures which are sensitive to systematic pattern errors. This information can be used by the design engineer to amend the design rules to disallow the suspected defect causing structures. Iterations of this technique will result in an integrated circuit design which is inherently more manufacturable and a manufacturing process with greater effective yield.

This and other needs are met by embodiments of the present invention which provide a method of detecting random layout structures sensitive to process induced pattern errors in semiconductor device manufacturing. The method comprises the steps of applying a first manufacturing process to a first wafer containing semiconductor devices, and applying a second manufacturing process to a second wafer containing semiconductor devices. The second manufacturing process is different from the first manufacturing process. The first and second wafers are compared by image subtraction to detect systematic pattern defects in the semiconductor devices of one of the first and second wafers.

One of the advantages of the present invention is the ability to detect repeating systematic pattern defects from wafer to wafer which were formerly undetectable using conventional approaches. With the advent of the present invention, the detection of repeating systematic pattern errors does not rely on the use of manual optical inspection or examination of electrical performance of test structures in areas merely suspected of being defective.

The earlier stated needs are met by another embodiment of the present invention which provides an apparatus for detecting random layout structures sensitive to process induced pattern errors in semiconductor device manufacturing. The apparatus comprises a processing system that performs a first processing step on a first wafer and a second processing step on a second wafer, the first and second processing steps being similar to, but not the same as, each other. An image subtraction defect detection device scans the first and second wafers and subtracts the scanned images of the first and second wafers from each other to identify defects in one of the first and second wafers.

Another embodiment of the invention also satisfies the earlier stated needs. In this embodiment, a method of designing circuitry of a semiconductor device manufactured on a wafer is provided. This method comprises the steps of laying out a circuit in accordance with an initial set of design rules and producing a control wafer in accordance with the initial set of design rules, employing a first manufacturing process. A second wafer is produced in accordance with the initial set of design rules, employing a second manufacturing process different from the first manufacturing process. The control wafer and the second wafer are then compared by image subtraction defect detection to detect systematic pattern defects in the circuitry of the second wafer. The initial set of design rules are then altered to prevent the detected systematic pattern defects in the circuitry of subsequently produced wafers.

A distinct advantage of the invention is the ability to optimize processing of the manufacture of semiconductor wafers by varying processing parameters to identify what stages of processing cause defects, and determine processing margins. The present invention makes defects more visible to inspection devices so that improvements can be made to the design, allowing the product to be inherently more manufacturable. This is achieved by making a comparison between the wafers produced by the two processes, one creating no defect and the other creating a defect. The design rules are altered to avoid the defects and thereby increase the processing margins and improve yields.

The foregoing and other features, aspects and advantages of the present invention will become more apparent from the following detailed description of the present invention when taken in conjunction with the accompanying drawings.

BRIEF DESCRIPTION OF THE DRAWINGS

FIG. 3 is a block diagram of a manufacturing arrangement with a plurality of processing stations constructed in accordance with an embodiment of the invention.

FIG. 4 is a block diagram of a defect detection arrangement constructed in accordance with an embodiment of the present invention.

DETAILED DESCRIPTION OF AN ILLUSTRATIVE EMBODIMENT

Figure 1:
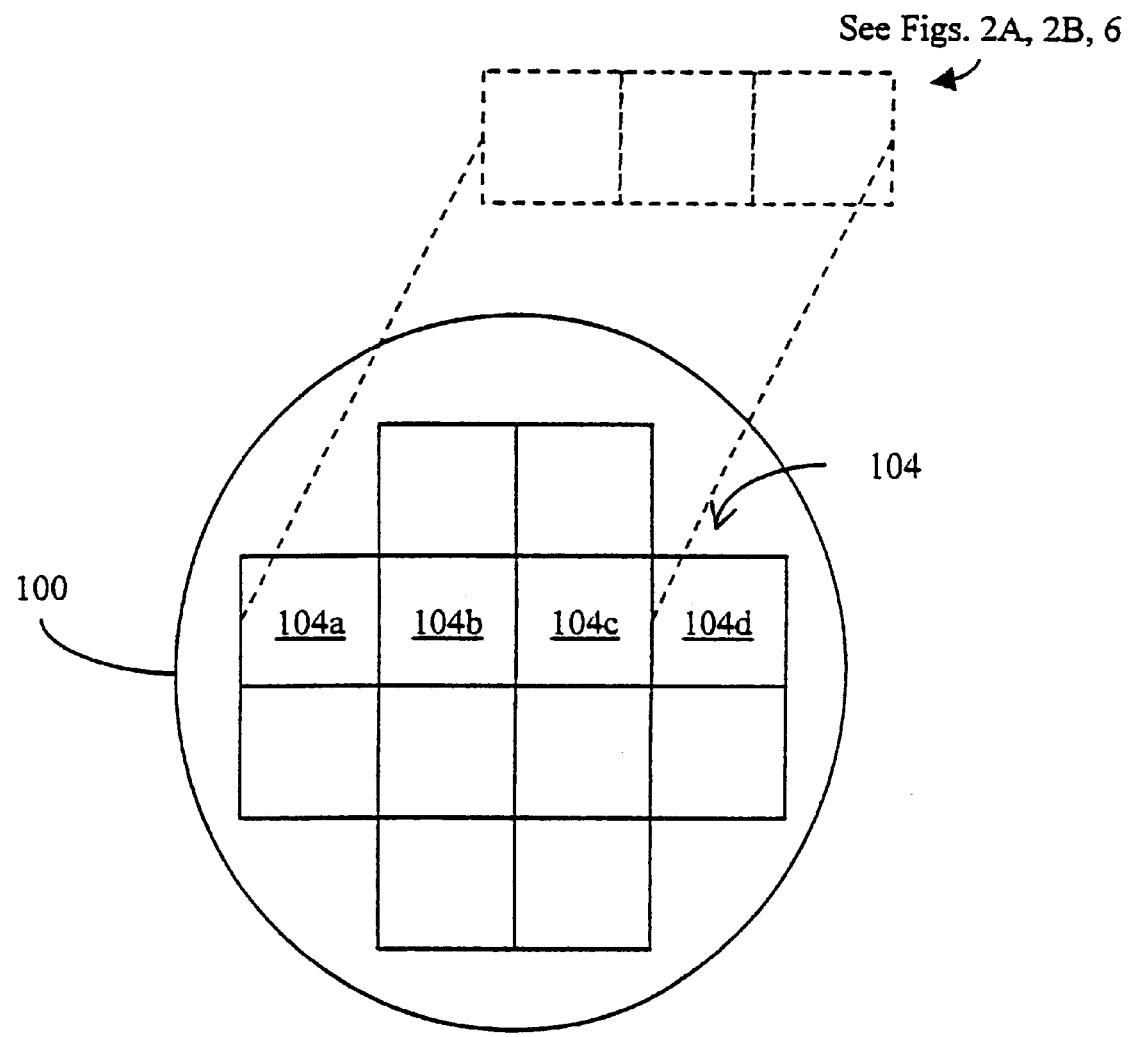
FIG. 1 is a schematic depiction of a semiconductor wafer illustrating regions to be inspected for defects.

The present invention will be described in the context of the manufacture of semiconductor devices. This is exemplary only, however, as the method of the invention is applicable to the manufacture of other types of products produced by one or more processing steps, using an automatically controlled processing tool.

FIG. 3 is a block diagram of a processing system 310 constructed in accordance with an embodiment of the present invention. The processing system 310 has a plurality of processing stations 312 that perform different steps of a manufacturing process. A shop floor system controller 314 communicates with the processing stations 312 to control the overall manufacturing processing of, for example, semiconductor wafers 100.

FIG. 4 is a block diagram of a defect detection arrangement constructed in accordance with an embodiment of the present invention. Wafer 100b is shown from a perspective view. In the case of semiconductor processing, processing system 310 performs conventional or state of the art processing operations on wafer 100b as indicated graphically by an arrow. Processing system 310 is also interconnected to an image subtraction defect detection system 400, such as those produced by KLA/Tencor for detecting defects in semiconductor processing as described in more detail below.

Defect detection system 400 includes a camera 410 which is connected to a computer 412 that together operate to gather images of portions of wafer 100b. Computer 412 controls camera 410 so that images are gathered of various layout structures (e.g., 108a, 108b) located within wafer 100b. Camera 410 focuses on a plurality of portions such as portions 420 and 422.

A memory 414 (such as a hard disk drive or DVD read-writable memory) stores the digitized images of the wafer. In the present application, the images of one wafer, or portions thereof, are stored. These stored images will be compared to images obtained from the scan of a second wafer 100b.

Figure 2A:
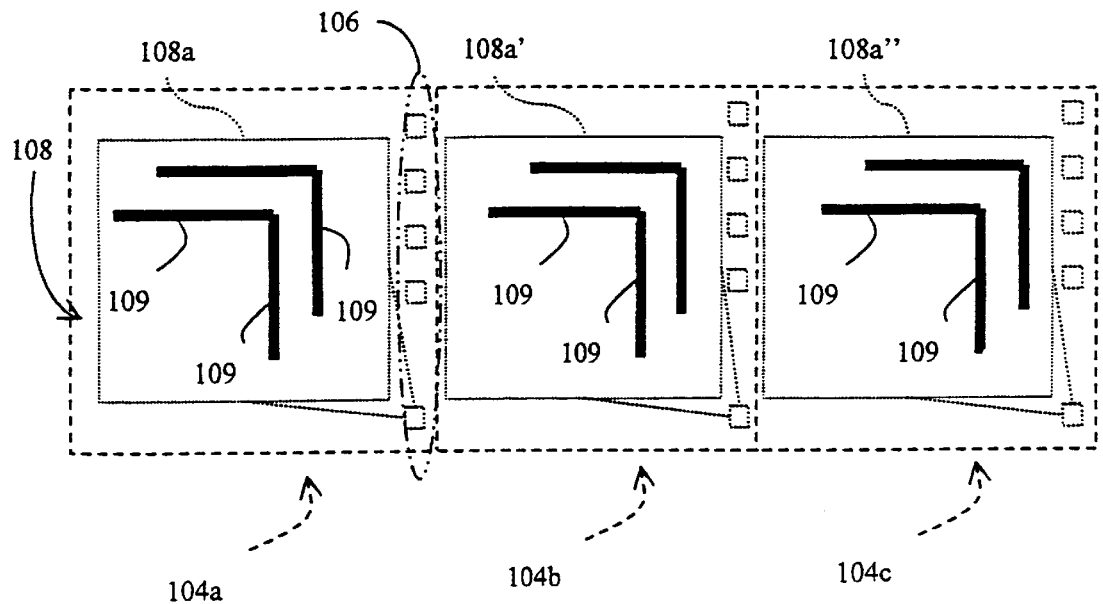
FIG. 2A is a block diagram of a region shown in FIG. 1 illustrating typical layout structures repeated within dies of a control semiconductor wafer.
Figure 2B:
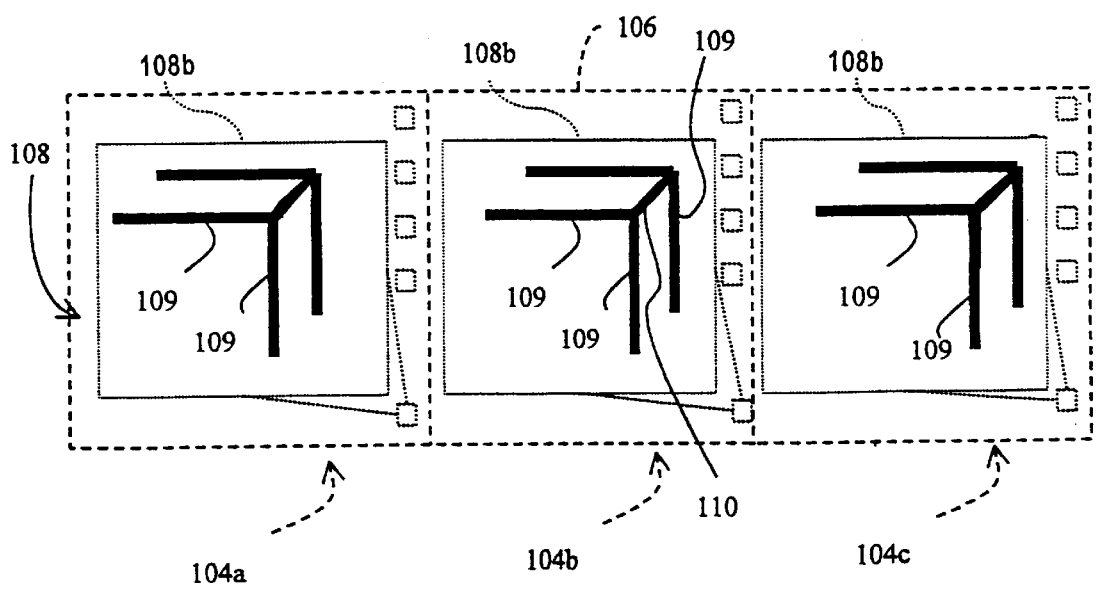
FIG. 2B is a block diagram of a region shown in FIG. 1 illustrating typical layout structures contained within dies of a semiconductor wafer that have a repeating systematic pattern defect.

In image subtraction defect detection, each portion 420 having layout structure 108b is compared to a corresponding portion 420 of a second wafer 108b. The corresponding portion is intended to include a structure identical to structure 108a or is caused to be different by a change in a manufacturing process step applied respectively to the first and second wafers. An image analyzer 424 compares the images of the structures intended to be identical, and performs image subtraction to determine if, for example, any structures FIGS. 2A and 2B) exist in one structure that are not present in the other. Image subtraction comprises forming images of each portion, for example using a binary representation where 0 represents background and 1 represents an element (e.g., path 109) detected by the camera, at each pixel location in the field of view of the camera. Subtracting the values at each corresponding pixel location in the two images determines the differences between the images. These differences identify defects or errors that occurred in processing as a result of a defective design, or improper processing carried out by processing system 310.

Performing image subtraction defect detection from wafer to wafer in accordance with the present invention permits systematic pattern defects to be detected. The variations in processing employed to produce the test wafers to be compared to a control wafer establish processing margins, or may be used to alter the design rules. As an example, assume that a control wafer is exposed to a particular etchant for five minutes. First and second test wafers may be exposed to the etchant for four and six minutes respectively, to under-etch and over-etch the test wafers. The wafer to wafer image subtraction defect detection of the present invention detects the effects of under-etching and over-etching on the structures contained in the wafers. If defects do not exist in the under-etched and over-etched wafers, then the process margins for this etching step may be expanded to between four and six minutes.

More importantly, the wafer to wafer image subtraction defect detection method of the present invention allows the design rules to be altered in order to provide greater process margins, and to detect layout structures that are problematic. For example, assume that a particular design rule permits the corner of a right-angled line to be a certain distance away from the corner of another right-angled line. However, it is determined through the wafer to wafer image subtraction defect detection method of the present invention that under-etching (e.g. four minutes instead of five minutes) produces an undesirable bridge between the lines, as in FIG. 2b. Once this problem in the design layout is detected, the design rules can be altered so that the structure produced according to the altered design rules will not be as adversely affected by under-etching. The separation between two right-angle lines may be required to be greater, in order to allow a degree of under-etching and thereby increase the processing margins.

In the above manner, the design layout and the design rules that cause such a layout to be produced are tested, and altered when proven to be necessary to increase processing margins. An important advantage of increased processing margins is the favorable effect this has on improving the yield. Since the altered design rules permit a wider variation in processing parameters, slight variations that occur during processing from wafer to wafer will not produce defects, if the variations fall within the processing margins established in accordance with the present invention.

Figure 5:
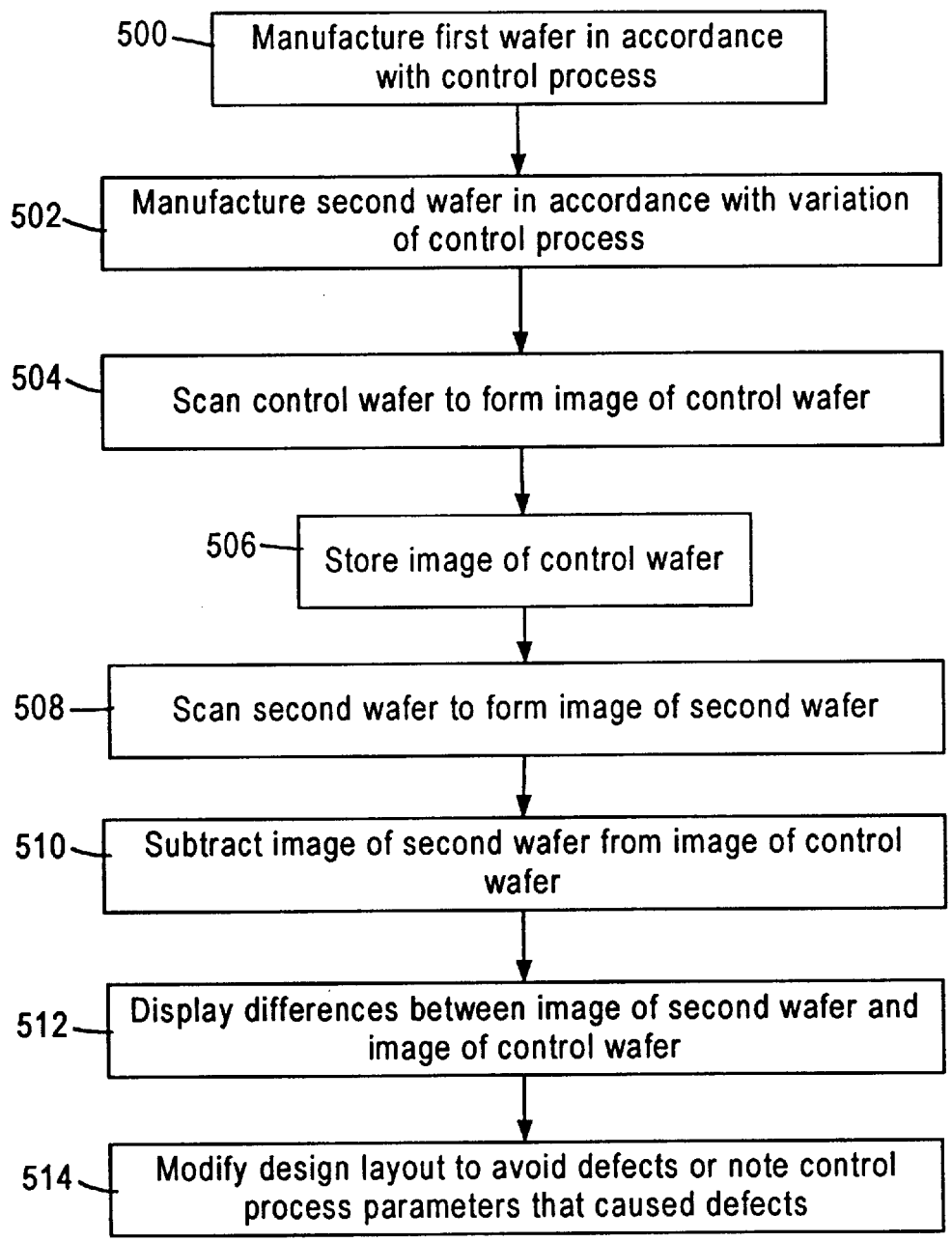
FIG. 5 is a flow chart of a method for performing systematic pattern defect detection in accordance with an embodiment of the present invention.

FIG. 5 is a flow chart depicting a wafer to wafer image subtraction defect detection method in accordance with embodiments of the present invention. In step 500 a first wafer, which may be considered a "control wafer", is produced in accordance with a control process. The wafer has dies with circuit layouts produced in accordance with a set of design rules appropriate for automatic design layout. In step 502, a second wafer is produced, but an altered process is employed to produce this second wafer. Variations may be made in one or more of a number of different processing steps, such as photolithography, etching, polishing, etc. However, the circuit layout in the dies of this second wafer are the same as the first wafer, so that the effect of process variations on the structure produced in accordance with the initial set of design rules can be determined.

The first wafer, i.e., the control wafer, is scanned in step 504, employing the defect detection system 400 of FIG. 4. Images of the entire wafer, or selected portions thereof, are digitized and stored in memory 414, as depicted in step 506. Unlike conventional inspection methodologies, which only compare images from the same wafer, the method of the present invention compares the images from different wafers. Hence, the memory 414 needs to retain the digitized images of the control wafer during the changing of the wafers in the defect detection system 400, and during scanning of the new wafer.

The second wafer is scanned in step 508 by the defect detection system 400 to form a digitized image of the second wafer, or portions thereof. The second image is compared to the stored first image (the control image) by the image subtraction method, in step 510. The differences between the two images are noted and stored, and may be displayed in step 512. In different embodiments of the invention, the second image is stored before comparison, so that two stored images are compared. In other embodiments, which are less memory-intensive, the second image is compared with the stored image (by the image analyzer 424) as the second wafer is being scanned. Only the differences between the two images are stored. This embodiment avoids storing an entire second image in memory.

With the differences between the control image and the second image displayed, defects in the second wafer caused by the effect of the processing variation on the design layout are made apparent to the circuit designer. In order to provide increased margins and improve yield, the circuit designer modifies the design rules to avoid structures associated with the defects produced as a result of the processing variations. This is represented by step 514 in FIG. 5.

The present invention has the advantage of employing existing components to provide wafer to wafer comparisons. Comparing structures on a wafer by wafer basis avoids the need for additional masking steps to mask portions of a wafer to allow different processing on the masked and unmasked portions. Also, effects on the wafer of variation in processing will more accurately reflect the effects of variations on production wafers. This is because a test wafer which is subjected to two cycles of the same processing step, one cycle varying from the other cycle, may respond differently than a wafer subjected to only a single cycle.

With the present invention, the effects of alterations made from a control process can be determined by a wafer to wafer inspection that detects differences between the wafers. In this way, the automated design rules that create the layout in which defects are detected may be altered to avoid the defects and expand processing margins. This alteration in design rules has a favorable impact on production yields.

Although the present invention has been described with the example of semiconductor wafer manufacturing applying an etching technique, the invention is applicable to identifying defects and variations caused by processing differences in other types of manufacturing techniques, such as epitaxy, oxidation, deposition (chemical vapor, physical), sputtering, diffusion, ion implantation, lithography.

Although the present invention has been described and illustrated in detail, it is to be clearly understood that the same is by way of illustration and example only, and is not to be taken by way of limitation, the spirit and scope of the present invention being limited only by the terms of the appended claims.

What is claimed is:

1. A method of detecting random layout structures sensitive to process induced pattern errors in semiconductor device manufacturing, the method comprising the steps of:

applying a first manufacturing process to a first wafer containing semiconductor devices;

applying a second manufacturing process to a second wafer containing semiconductor devices, the second manufacturing process being different from the first manufacturing process;

comparing the first and second wafers by image subtraction to detect systematic pattern defects in the semiconductor devices of one of the first and second wafers.

2. The method of claim 1, wherein the first manufacturing process is a standard manufacturing process and the second manufacturing process is a non-standard process that is substantially similar to, but not the same as, the first manufacturing process.

3. The method of claim 2, further comprising applying other manufacturing processes to other wafers containing semiconductor devices, wherein the other manufacturing processes are non-standard processes that are substantially similar to, but not the same as, the first and second manufacturing processes and each other, and comparing the first wafer with the other wafers by image subtraction.

4. The method of claim 2, further comprising scanning the first wafer to which the standard manufacturing process has been applied to create a digitized image of at least a portion of the first wafer and storing the digitized image.

5. The method of claim 4, wherein the step of comparing the first and second wafers includes scanning the second wafer to create a digitized image of at least a portion of the second wafer and subtracting the digitized image of the second wafer portion from the digitized image of the first wafer portion to detect differences in the digitized images.

6. The method of claim 5, further comprising altering design layout rules in response to the detection of differences in the digitized images.

7. An apparatus for detecting random layout structures sensitive to process induced pattern errors in semiconductor device manufacturing, comprising:

a processing system that performs a first processing step on a first wafer and a second processing step on a second wafer, the first and second processing steps being similar to, but not the same as, each other; and an image subtraction defect detection device which scans the first and second wafers and subtracts the scanned images of the first and second wafers from each other to identify defects in one of the first and second wafers.

8. The apparatus of claim 7, wherein the image subtraction defect detection device includes a camera to scan the wafers and produces a digitized signal, a processor that controls the scanning of the wafers by the scanner; a memory that stores the scanned image of at least one of the first and second wafers; and an image analyzer that compares the stored scanned image with the scanned image of the other one of the first and second wafers to detect differences between the scanned images of the first and second wafers.

9. A method of designing circuitry of a semiconductor device manufactured on a wafer, comprising the steps of:

laying out a circuit in accordance with an initial set of design rules;

producing a control wafer in accordance with the initial set of design rules, employing a first manufacturing process;

producing a second wafer in accordance with the initial set of design rules, employing a second manufacturing process different from the first manufacturing process;

comparing the control wafer and the second wafer by image subtraction defect detection to detect systematic pattern defects in the circuitry of the second wafer; and altering the initial set of design rules to prevent the detected systematic pattern defects in the circuitry of subsequently produced wafers.

10. The method of claim 9, wherein the step of comparing includes scanning the control wafer to create a digitized image of at least a portion of the control wafer and storing the digitized image.

11. The method of claim 10, wherein the step of comparing includes scanning the second wafer to create a digitized image of at least a portion of the second wafer and subtracting the digitized image of the second wafer from the digitized image of the control wafer to detect differences in the digitized images.

* * * * *